/

US007517983B2

(12) United States Patent
Lopes et al.

(10) Patent No.: US 7,517,983 B2
(45) Date of Patent: Apr. 14, 2009

(54) HYDRAZINES AND DERIVATIVES PRODUCTION PROCESS FROM HYDRAZINES AND DICARBOXYLIC ACID

(75) Inventors: Cláudio Cerqueira Lopes, Rio de Janeiro (BR); Rosângela Sabattini Capella Lopes, Rio de Janeiro (BR); Jarí Nobrega Cardoso, Rio de Janeiro (BR); Jacqueline Alves da Silva, Rio de Janeiro (BR); Letícia Gomes Ferreira, Rio de Janeiro (BR)

(73) Assignee: Universidade Federal Do Rio De Janeiro-UFRG, Rio de Janeiro (BR)

( * ) Notice: Subject to any disclaimer, the term of this patent is extended or adjusted under 35 U.S.C. 154(b) by 101 days.

(21) Appl. No.: 10/595,943

(22) PCT Filed: Nov. 25, 2004

(86) PCT No.: PCT/BR2004/000236

§ 371 (c)(1),
(2), (4) Date: May 22, 2006

(87) PCT Pub. No.: WO2005/051870

PCT Pub. Date: Jun. 9, 2005

(65) Prior Publication Data

US 2007/0128680 A1     Jun. 7, 2007

(30) Foreign Application Priority Data

Nov. 25, 2003  (BR)  .................................... 0307864

(51) Int. Cl.
*C07D 237/32*  (2006.01)
*C07D 237/04*  (2006.01)
*C07D 231/28*  (2006.01)

(52) U.S. Cl. .................... 544/240; 544/237; 548/366.4; 548/366.7; 548/367.1

(58) Field of Classification Search ................. 544/235, 544/237, 240; 548/366.4, 366.7, 367.1
See application file for complete search history.

(56) References Cited

U.S. PATENT DOCUMENTS

2007/0185191 A1*  8/2007  Araldi et al. ................. 514/438

OTHER PUBLICATIONS

Barakat, et al., Journal of the Chemical Society, 1955, pp. 3299-3300.*

* cited by examiner

*Primary Examiner*—Mark L Berch
*Assistant Examiner*—Cecilia M Jaisle
(74) *Attorney, Agent, or Firm*—Laurence P. Colton; Smith, Gambrell & Russell

(57) ABSTRACT

The present invention describes a process to form hydrazides from the reaction of a hydrazine and a dicarboxylic, using a Lewis acid as a main reagent of the reaction. The reaction occurs in a safe reactional environment, utilizing smooth conditions, neither involving high temperatures nor high pressures, producing the desired products with high yields, between 90-95%. The invention also describes a kit for utilization of chemiluminescent substances, comprised of two solutions.

16 Claims, No Drawings

HYDRAZINES AND DERIVATIVES PRODUCTION PROCESS FROM HYDRAZINES AND DICARBOXYLIC ACID

FIELD OF THE INVENTION

The present invention describes a new process that favors the production of hydrazides from dicarboxylic acids, using a Lewis acid. More specifically, the present invention is directed to the formation of phtalazides, for example luminol, using as Lewis acid a halide donor, more specifically chloride, for example niobium pentachloride. The process provides a global yielding well above traditional techniques yielding, as well as easy execution, without the need of drastic reactional conditions.

BACKGROUND OF THE INVENTION

It is extremely desirable and convenient to have secure methods for the reliable trace detection of substances in liquids, especially body fluids, where the presence of a concentration as low as $10^{-11}$ M of a substance may be potentially pathogenic.

Classical methods of detection in liquids are based on reaction mechanisms where either the appearance of a product or the disappearance of a reagent can be measured. Greater importance is given to chemiluminescent compounds, capable of producing light when in favorable conditions.

The chemiluminescence is a method based on certain substances characteristic of emitting light when in presence of the compound to be analyzed. It has applications in forensics, diagnosis and quality control fields, being capable of detecting traces of compounds. One example of a commonly used chemiluminescent substance in criminal investigations is luminol, capable of detecting blood stains hidden in suspicious locations, such as crime scenes. The mechanism of action of luminol is based on the reaction below, where the addition of hydrogen peroxide is capable of oxidizing the luminol in a basic medium, generating light. However, the reaction below needs a catalyst, which will be the iron (Fe) present on erythrocyte's hemoglobin of the blood. Hence, when a basic luminol solution is put in contact with a hydrogen peroxide solution with Fe, an intense glow will be produced, confirming the presence of the compound.

There are many applications for chemiluminescent substances besides forensics. Recently, there has been a demand and production increase, especially for entertainment and in accidents preventions industries. A number of accessories, such as bracelets, necklaces, earrings, plastic teeth frame, cups etc, are frequently used in events, residences, night clubs, theaters, stadiums, music festivals, rodeos and many others, drawing the attention of the public with the intense chemiluminescence reaction glow. Safety flares are used by scuba-divers in deep waters and poor visibility, especially in the maintenance of underwater industrial petrol plants maintenance, or by the police and fire department in case of night accidents with intense fog or in unfavorable weather conditions on roads and large avenues or by the coast guard, helping night sailing on rivers, bays and near the coast. These are some examples of the many applications of the chemiluminescent substances industrially produced by the process described on the present invention, specially the luminol.

Luminol and its derivatives synthesis process include, among other steps, the reaction of a dicarboxylic acid with a hydrazine. This stage is usually difficult to accomplish, since drastic conditions are needed and the yield is not significantly high. Some documents propose solutions to this stage.

British patent GB 1,100,911 is the first to describe the synthesis of phtalazine derivatives. Among the proposed processes, it uses a mixture of a dicarboxylic acid and a hydrazine, the mixture being heated under reflux for 4 hours. The solution is cooled and water and HCl are added until pH 7. The solid formed is recrystallized in hot water.

American patent U.S. Pat. No. 4,226,992 performs the formation of the phtalazide from a dicarboxylic acid and a hydrazine in methanol under reflux for 3 hours. After cooling, the mixture is evaporated until dryness in a rotoevaporator, and the crystalline residue dried overnight at 80° C. under vacuum.

American patent U.S. Pat. No. 4,226,993 describes the reaction of a phtalimide with a hydrazine, in ethanol for 2 hours under reflux, followed by cooling and rest overnight. After evaporation in rotoevaporator under reduced pressure, the solid was dried at 110° C. for 8 hours under a pressure of 0.1 mmHg. The solid residue was stirred for 90 minutes in HCl 10%, filtered and neutralized with KOH, and the precipitated was filtered, dried and recrystallized in aqueous dimethyl formamide One document describing a technique similar to the present invention's is American patent U.S. Pat. No. 6,489,326. It describes an extremely dangerous and complex production process of a hydrazide from the 3-nitro-phtalic anhydride and hydrazine. In spite of presenting excellent yields, between 85 and 90%, the reaction involves a Ni-Raney catalyst, gas generation, such as $N_2$ and $H_2$, and is extremely exothermic, reaching temperatures of 285-90° C.

Unlike all the processes described above, the present invention uses a halide donor, more specifically chloride,

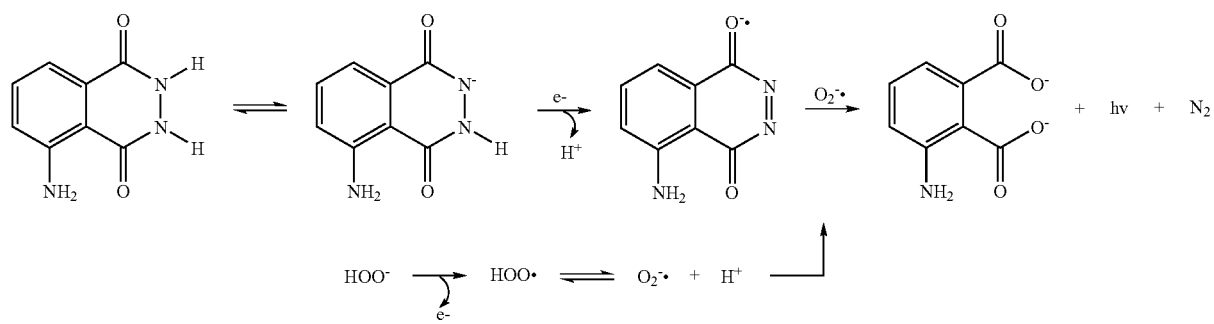

even more specifically niobium pentachloride in dioxane, that promotes a smooth reaction, easy controlled and capable of generating 90-95% yield.

Niobium pentachloride is a known Lewis acid, used as a catalyst for cyclotrimetrization reactions, for example, reactions described in document WO 91/09066. Regarding the synthesis of organic compounds, an important document, though not relevant, is document U.S. Pat. No. 4,349,471, which describes the synthesis of sulfonic acid halides and aromatic carboxylic acids halides. The referred reaction involves the use of a Lewis acid, for example niobium pentachloride.

However, the reaction of the present invention is completely different from the reactions described on the above mentioned documents, and therefore the use of a Lewis acid halide donor, more specifically chloride, for example niobium pentachloride, aiming hydrazides synthesis from dicarboxylic acids and hydrazines have never been described before, being the present invention therefore new.

OBJECT OF THE INVENTION

It is an object of the present invention to provide an alternative process for the synthesis of hydrazides from dicarboxylic acids and hydrazines.

It is an additional object of the present invention to provide a process for the synthesis of hydrazides in safe and smooth reactional conditions, without gas or heat liberation and having an excellent yield.

It is still an object of the invention to provide economically more viable hydrazides synthesis.

It is an object of the present invention to provide a process of synthesis of hydrazides, where such process is based on the use of a Lewis acid as a halide donor. More specifically, the process is based on the use of a Lewis acid as a chloride donator. More specifically still, the Lewis acid is niobium pentachloride.

It is an additional object of the present invention to provide a preparation process of luminol based on the production of a hydrazide, where the Lewis acid is a chloride donator, more specifically still, the Lewis acid is niobium pentachloride.

It is an additional object of the present invention to provide a kit for the use of a chemiluminescent composition, more specifically luminol, where such kit provides a long-lasting luminescence and easy application without the need of ultraviolet light.

DETAILED DESCRIPTION OF THE INVENTION

The present invention presents innovative characteristics in an alternative process for hydrazide production, based in the use of halide donors as catalysts, resulting in reactions with better yields than the available methods. The present invention also provides a new process of luminol synthesis which is cheaper and economically viable.

The reaction described aims a production of a hydrazide from the reaction of a dicarboxylic acid of a general formula (I):

wherein R1 can be hydrogen, alkyl, alkenyl, alkinyl, phenyl, aromatic heterocyclic ring containing as heteroatom S, O and/or N, heterocyclic non-aromatic ring containing as heteroatom S, O and/or N, cycloalkyl containing from 3 to 8 carbon atoms, cycloalkenyl containing from 3 to 8 carbon atoms, cycloalkinyl containing from 3 to 8 carbon atoms; all the described groups can be further substituted and/or branched;

n varies from 1 to 2;

with a hydrazine of general formula (II):

wherein R2 and R3 are, independently, hydrogen, alkyl, alkenyl, alkinyl, phenyl, heterocyclic aromatics containing as heteroatom S, O and/or N, heterocyclic non-aromatics containing as heteroatom S, O and/or N, cycloalkyl containing from 3 to 8 carbon atoms, cycloalkenyl containing from 3 to 8 carbon atoms, cycloalkinyl containing from 3 to 8 carbon atoms;

in the presence of a chloride donor reagent.

Additionally, the present invention aims the production of a hydrazide from the reaction of a dicarboxylic acid of general formula (III):

wherein A can be an aromatic heterocyclic ring containing from 4 to 8 atoms, a non-aromatic ring containing from 4 to 8 atoms, an aromatic heterocyclic ring containing from 4 to 8 atoms, wherein the heteroatom is S, O and/or N, a non-aromatic heterocyclic ring containing from 4 to 8 atoms, wherein the heteroatom is S, O and/or N; all the described groups can be further substituted and/or branched;

ring A can further have 1 or more aromatic, non-aromatic, aromatic heterocyclic, non-aromatic heterocyclic rings and mixture thereof, coupled, wherein the heteroatom can be N, O, and/or S;

X can be C or N;

Y can be C or N;

with a hydrazine of general formula (II):

wherein R2 and R3 are, independently, hydrogen, alkyl, alkenyl, alkinyl, phenyl, heterocyclic aromatics containing as heteroatom S, O and/or N, heterocyclic non-aromatics containing as heteroatom S, O and/or N, cycloalkyl containing from 3 to 8 carbon atoms, cycloalkenyl containing from 3 to 8 carbon atoms, cycloalkinyl containing from 3 to 8 carbon atoms;

in the presence of a chloride donor reagent.

The reaction occurs at room temperature, with excellent yielding. Additionally, it is possible to use a dicarboxylic acid of general formula (I) or (III) suspended in an organic solvent.

The Lewis acid halide donator is chosen from the groups comprising aluminum chloride, antimony trichloride, antimony pentachloride, arsenic trichloride, arsenic pentachloride, beryllium chloride, bismuth trichloride, boron trifluoride, boron trichloride, cadmium chloride, copper chloride (I), copper chloride (II), cobalt chloride, chromo trichloride, gallium chloride, iron chloride (III), mercury chloride (II), magnesium chloride, magnesium bromide, nickel chloride, niobium pentachloride, titanium dichloride, titanium trichloride, titanium tetrachloride, tellurium tetrachloride, uranium tetrachloride, zirconium tetrachloride, zinc chloride and mixture of them.

Suitable organic solvents for the dicarboxylic acid suspension can be selected among solvents of the prior art.

The followings examples are only illustrative, not limiting the present invention.

EXAMPLE 1

The synthesis of luminol as presented in this invention has four stages as showed in the following scheme:

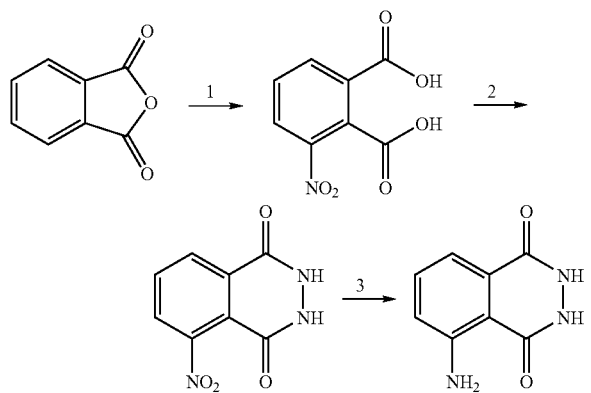

Reagents of stage 1 are $H_2SO_4$ and $HNO_3$, responsible for the nitration of phthalic anhydride in smooth conditions.

In stage 2, the inventive step is the use of niobium pentachloride in a suspension of 3-nitrophthalic acid in dioxane. After 30 minutes was added an aqueous hydrazine 40% solution obtaining the 5-nitro-2,3-dihidroftalizide-1,4-dione intermediate.

In a three-necked 100 mL flask, equipped with magnetic stirrer, reflux condenser and dry argon flow, were added 4.71 mmols of niobium pentachloride followed by the addition of 30.0 mL of dioxane and 1-nitro phthalic acid (14.13 mmols). After few minutes under vigorous agitation, a suspension is observed. Afterwards, it was added a 40% aqueous solution of hydrazine (37.68 mmols) in the mixture. In thirty minutes the temperature was raised slowly to 45-50° C. and the reaction time was extended more four hours. The mixture was cooled and the solids obtained were removed through filtration. The filtered was extracted with ethyl acetate (200.0 mL) and washed with a 5% solution of sodium bicarbonate (60.0 mL), saturated solution of sodium chloride (2×60.0 mL) and distilled water (3×60.0 mL). The organic phase was dried with anhydrous sodium sulphate and evaporated under vacuum and recrystallized in ethanol/ distillated water resulting in luminol in a 90-95% yield.

The niobium pentachloride in this process is converted to niobium pentoxide. However, the formation of 1-nitro-phthalic acid chloride can be admitted from the correspondent niobate through a nucleophilic attack by the chlorides generated in the reactional medium from the niobium pentachloride, to this reagent earning the property of chloride donor in this transformation.

In the 3rd stage, a simple reduction reaction was capable of reducing the nitro group to amine group. In this case, it can be used reducing agents like sodium dithionite in acid medium followed by the addition of acetic acid. This reduction can also be promoted by the hydrogenation process containing palladium over carbon (10%) in solvents like dioxane and acetic acid. The final product, luminol, is obtained in quantitative yield.

EXAMPLE 2

Additionally, the invention provides a kit comprising a solution of one chemiluminescent substance obtained by the process described above, being the kit composed by two separated solutions, namely solution A and solution B.

Solution A comprises an alkaline solution of luminol, where the concentration of luminol ranges from 0.75 to 7.0 g/L, preferably 5.0 g/L. Solution B comprises hydrogen peroxide in water, wherein the hydrogen peroxide concentration ranges from 1.0 to 5.0%, preferably 3,0%. The solution pH ranges from 8 to 14, preferably 13.6. Any alkalinizing agent can be used, with the proviso that the final pH ranges between 8 and 14. It is known by alkalinizing agent any substance capable of generate hydroxyl ions when in solution. The preferred alkalinizing agents are alkali metals hydroxides, and its concentration can range from 0.05M to 3.0M, preferably from 0.1M to 0.5M.

The procedure requires the simultaneously application of solutions A and B in the local where the chemiluminescent reaction will occur. If the reaction occurs, an intense blue coloration will be observed, visible in dark environment not being necessary the use of UV lamps. Otherwise no intense coloration will be observed.

The principal advantage of this kit is the durability of reagents present at solutions A and B. Conventional kits are presented as a mixture of solids generally containing luminol, sodium carbonate, sodium borate etc, which after solubilization in distilled water produce one solution to obtain the chemiluminescent reaction which do not last longer that the solution here presented. The kit presented in this invention has the advantage of providing a long-lasting reaction and not requiring the use of UV light to observe the color appearance. It is due to the stability provided by the alkaline medium to the hydrogen peroxide, slowing its degradation.

The invention claimed is:

1. Process to produce hydrazides, comprising the reaction of a dicarboxylic acid having general formula (I):

$(R^1CH)_n(COOH)_2)$         (I)

wherein R1 is selected from the group consisting of hydrogen, alkyl, alkenyl, alkynyl, phenyl, aromatic heterocyclic ring having a heteroatom selected from the group consisting of S, O, and N, heterocyclic non-aromatic ring having a heteroatom selected from the group consisting of S, O and N, cycloalkyl containing from 3 to 8 carbon atoms, cycloalkenyl containing from 3 to 8 carbon atoms, and cycloalkynyl containing from 7 to 8 carbon atoms; and wherein the R1 groups can be further substituted and/or branched;

n is 1 or 2;

with a hydrazine of general formula (II)

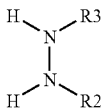

wherein R2 and R3 are, independently, selected from the group consisting of hydrogen, alkyl, alkenyl, alkynyl, phenyl, heterocyclic aromatics having a heteroatom selected from the group consisting of S, O and N, heterocyclic non-aromatics having a heteroatom selected from the group consisting of S, O and N, cycloalkyl containing from 3 to 8 carbon atoms, cycloalkenyl containing from 3 to 8 carbon atoms, and cycloalkynyl containing from 7 to 8 carbon atoms;
wherein the hydrazine is soluble in water or in a reaction solvent;
wherein the reaction occurs at room temperature;
in the presence of a Lewis acid.

2. Process to produce hydrazides, comprising the reaction of a dicarboxylic acid having general formula (III):

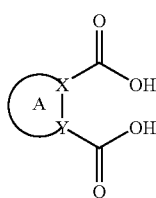

wherein A is selected from the group consisting of an aromatic heterocyclic ring containing from 4 to 8 atoms, and a non-aromatic heterocyclic ring containing from 4 to 8 atoms, wherein the heteroatom is selected from the group consisting of S, O and N, and wherein A can be further substituted and/or branched;
  ring A can further have 1 or more fused ring, wherein the ring is aromatic, non-aromatic, aromatic heterocyclic, non-aromatic heterocyclic and mixtures thereof, and wherein the heteroatom is selected from the group consisting of N, O, and S;
  X is C or N;
  Y is C or N;
  with a hydrazine of a general formula (II)

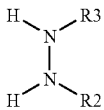

wherein R2 and R3 are, independently, selected from the group consisting of hydrogen, alkyl, alkenyl, alkynyl, phenyl, heterocyclic aromatics having a heteroatom selected from the group consisting of S, O and N, heterocyclic non-aromatics having a heteroatom selected from the group consisting of S, O and N, cycloalkyl containing from 3 to 8 carbon atoms, cycloalkenyl containing from 3 to 8 carbon atoms, cycloalkynyl containing from 7 to 8 carbon atoms;
  wherein the hydrazine is soluble in water or in a reaction solvent;
  wherein the reaction occurs at room temperature;
  in the presence of a Lewis acid.

3. Process according to claim 1, wherein the Lewis acid is a halide donator.

4. Process according to claim 3, wherein the Lewis acid is a halide donator selected from the group consisting of aluminum chloride, antimony trichloride, antimony pentachloride, arsenic trichloride, arsenic pentachloride, beryllium chloride, bismuth trichloride, boron trifluoride, boron trichloride, cadmium chloride, copper chloride (I), copper chloride (II), cobalt chloride, chromo trichloride, gallium chloride, iron chloride (III), mercury chloride (II), magnesium chloride, magnesium bromide, nickel chloride, niobium pentachloride, titanium dichloride, titanium trichloride, titanium tetrachloride, tellurium tetrachloride, uranium tetrachloride, zirconium tetrachloride, and mixtures thereof.

5. Process to produce hydrazides, comprising the reaction of a dicarboxylic acid having general formula (I):

$$(R^1CH)_n(COOH)_2 \quad (I)$$

wherein R1 is selected from the group cosisting of hydrogen, alkyl, alkenyl, alkynyl, phenyl, aromatic heterocyclic ring having a heteroatom selected from the group consisting of S, O and N, heterocyclic non-aromatic ring having a heteroatom selected from the group consisting of S, O and N, cycloalkyl containing from 3 to 8 carbon atoms, cycloalkenyl containing from 3 to 8 carbon atoms, and cycloalkynyl containing from 7 to 8 carbon atoms; and wherein the R1 groups can be further substituted and/or branched;
  n is 1 to 2;
  with a hydrazine of general formula (II)

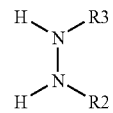

wherein R2 and R3 are, independently, selected from the group consisting of hydrogen, alkyl, alkenyl, alkynyl, phenyl, heterocyclic aromatics heteroatom selected from the group consisting of S, O and N, heterocyclic non-aromatics having a heteroatom selected from the group consisting of S, O and N, cycloalkyl containing from 3 to 8 carbon atoms, cycloalkenyl containing from 3 to 8 carbon atoms, and cycloalkenyl containing from 7 to 8 carbon atoms;
  wherein the hydrazine is soluble in water or in a reaction solvent;
  wherein the reaction occurs at room temperature;
  in the presence of a Lewis acid,
  wherein the halide donator Lewis acid is niobium pentachloride.

6. Process according to claim 1, wherein the dicarboxylic acid is suspended in an organic solvent.

7. Process according to claim 6, wherein the organic solvent Is an aprotic polar organic solvent.

8. Process according to claim 7, wherein the solvent is chosen from the group consisting of dioxane, acetone, methylpyrrolidone, dimethylsulfoxide, N, N-dimethylformamide, and mixtures thereof.

9. Process to produce hydrazides. comprising the reaction of a dicarboxylic acid having aeneral formula (I):

$$(R^1CH)_n(COOH)_2 \quad (I)$$

wherein R1 is selected from the group cosisting of hydrogen, alkyl, alkenyl, alkynyl, phenyl, aromatic heterocyclic ring having a heteroatom selected from the group consisting of S, O and N, heterocyclic non-aromatic ring having a heteroatom selected from the group consisting of S, O and N, cycloalkyl containing from 3 to 8 carbon atoms, cycloalkenyl containing from 3 to 8 carbon atoms, and cycloalkynyl containing from 7 to 8 carbon atoms; and wherein the R1 groups can be further substituted and/or branched;

n is 1 to 2;

with a hydrazine of general formula (II)

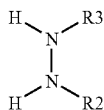

(II)

wherein R2 and R3 are, independently, selected from the group consisting of hydrogen, alkyl, alkenyl, alkynyl, phenyl, heterocyclic aromatics heteroatom selected from the group consisting of S, O and N, heterocyclic non-aromatics having a heteroatom selected from the group consisting of S, O and N, cycloalkyl containing from 3 to 8 carbon atoms, cycloalkenyl containing from 3 to 8 carbon atoms, and cycloalkenyl containing from 7 to 8 carbon atoms;

wherein the hydrazine is soluble in water or in a reaction solvent;

wherein the reaction occurs at room temperature;

in the presence of a Lewis acid, further comprising the reaction of 1-nitro-phtalic acid with the hydrazine in the presence of niobium pentachloride.

10. Process according to claim 9, wherein the Lewis acid is a halide donator.

11. Process according to claim 10, wherein the Lewis acid is a halide donator selected from the group consisting of aluminum chloride, antimony trichloride, antimony pentachloride, arsenic trichloride, arsenic pentachloride, beryllium chloride, bismuth trichloride, boron trifluoride, boron trichloride, cadmium chloride, copper chloride (I), copper chloride (II), cobalt chloride, chromo trichloride, gallium chloride, iron chloride (III), mercury chloride (II), magnesium chloride, magnesium bromide, nickel chloride, niobium pentachloride, titanium dichloride, titanium trichloride, titanium tetrachloride, tellurium tetrachloride, uranium tetrachloride, zirconium tetrachloride, and mixtures thereof.

12. Process according to claim 11, wherein the halide donator Lewis acid is niobium pentachloride.

13. Process according to claim 2, wherein the dicarboxylic acid is suspended in an organic solvent.

14. Process according to claim 13, wherein the organic solvent is an aprotic polar organic solvent.

15. Process according to claim 14, wherein the solvent is selected from the group consisting of dioxane, acetone, methylpyrrolidone, dimethylsulfoxide, N, N-dimethylformamide, and mixtures thereof.

16. Process to produce hydrazides, comprising the reaction of a dicarboxylic acid having general formula (III):

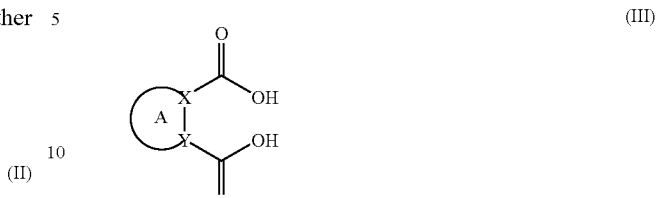

(III)

wherein A is selected from the group consisting of an aromatic heterocyclic ring containing from 4 to 8 atoms, and a non-aromatic heterocyclic ring containing from 4 to 8 atoms, wherein the heteroatom is selected from the group consisting of S, O and N, and wherein A can be further substituted and/or branched;

ring A can further have 1 or more fused ring, wherein the ring is aromatic, non-aromatic, aromatic heterocyclic, non-aromatic heterocyclic and mixtures thereof, and wherein the heteroatom is selected from the group consisting of N, O, and S;

X is C or N;

Y is C or N;

with a hydrazine of a general formula (II)

(II)

wherein R2 and R3 are, independently, selected from the group consisting of hydrogen, alkyl, alkenyl, alkynyl, phenyl, heterocyclic aromatics having a heteroatom selected from the group consisting of S, O and N, heterocyclic non-aromatics having a heteroatom selected from the group consisting of S, O and N, cycloalkyl containing from 3 to 8 carbon atoms, cycloalkenyl containing from 3 to 8 carbon atoms, cycloalkynyl containing from 7 to 8 carbon atoms;

wherein the hydrazine is soluble in water or in a reaction solvent;

wherein the reaction occurs at room temperature;

in the presence of a Lewis acid.

further comprising the reaction of 1-nitro-phtalic acid with the hydrazine in the presence of niobium pentachloride.

* * * * *

UNITED STATES PATENT AND TRADEMARK OFFICE
CERTIFICATE OF CORRECTION

PATENT NO. : 7,517,983 B2
APPLICATION NO. : 10/595943
DATED : April 14, 2009
INVENTOR(S) : Claudio Cerqueira Lopes et al.

It is certified that error appears in the above-identified patent and that said Letters Patent is hereby corrected as shown below:

On the Title Page Item (73)

"Assignee"

Universidade Federal Do Rio De Janeiro-UFRG" should read --"Universidade Federal Do Rio De Janeiro-UFRJ--

Signed and Sealed this

Thirtieth Day of June, 2009

JOHN DOLL
*Acting Director of the United States Patent and Trademark Office*